United States Patent
Sandifer et al.

(10) Patent No.: US 8,066,654 B2
(45) Date of Patent: Nov. 29, 2011

(54) ADJUSTABLE EXTENSION COMPRESSION POSTERIOR SPINAL ORTHOSIS AND METHOD

(75) Inventors: Alan T. Sandifer, Casselberry, FL (US); Shannon R. Schwenn, Deltona, FL (US)

(73) Assignee: Orthomerica Products, Inc., Orlando, FL (US)

( * ) Notice: Subject to any disclaimer, the term of this patent is extended or adjusted under 35 U.S.C. 154(b) by 0 days.

(21) Appl. No.: 12/670,847

(22) PCT Filed: Jul. 31, 2007

(86) PCT No.: PCT/US2007/074875
§ 371 (c)(1),
(2), (4) Date: Jan. 26, 2010

(87) PCT Pub. No.: WO2009/017499
PCT Pub. Date: Feb. 5, 2009

(65) Prior Publication Data
US 2010/0204630 A1    Aug. 12, 2010

(51) Int. Cl.
*A61F 5/00* (2006.01)
*A45F 3/08* (2006.01)
(52) U.S. Cl. .......................................... 602/19; 224/263
(58) Field of Classification Search ................. 224/628, 224/643, 644, 934, 153, 620, 627, 630–639, 224/261–263; 602/19, 5, 6, 1, 20, 32, 36
See application file for complete search history.

(56) References Cited

U.S. PATENT DOCUMENTS

| | | |
|---|---|---|
| 639,072 A | 12/1899 | Lyons |
| 709,055 A | 9/1902 | Sheldon |
| 1,316,915 A | 9/1919 | Meyer et al. |
| 1,755,641 A | 4/1930 | Foulke |
| 2,808,050 A | 10/1957 | Ward |
| 2,828,737 A | 4/1958 | Hale |
| 3,095,875 A | 7/1963 | Davidson et al. |
| 3,274,996 A | 9/1966 | Jewett |
| 3,351,053 A | 11/1967 | Stuttle |
| 3,771,513 A | 11/1973 | Velazquez |
| 3,945,376 A | 3/1976 | Kuehnegger |
| RE31,564 E | 4/1984 | Hendricks |
| 4,640,269 A | 2/1987 | Goins |
| 4,648,390 A | 3/1987 | Friddle |
| 5,120,288 A | 6/1992 | Sinaki |
| 5,135,471 A | 8/1992 | Houswerth |
| 5,548,843 A | 8/1996 | Chase et al. |
| 5,599,287 A | 2/1997 | Beczak, Sr. et al. |
| 5,674,187 A | 10/1997 | Zepf |
| 5,685,831 A | 11/1997 | Floyd |

(Continued)

OTHER PUBLICATIONS

Spinomed® brochure—Spinal orthosis for vertebral extension in osteoporosis, 1 page, 2007.

(Continued)

*Primary Examiner* — Patricia Bianco
*Assistant Examiner* — Tarla Patel (57) ABSTRACT

A spinal orthosis and method of applying extension and compression forces onto a user spine includes a lumbo-sacral compression unit conforming to a portion of a user's torso and exerting an encircling compressive force to provide a hydraulic lift. A posterior spinal frame member is secured by the lumbo-sacral compression unit to be cantilevered upward along the user's spine. A pair of adjustable shoulder strap assemblies are connected to an upper portion of the posterior spinal frame member and adjacent a lower portion of the posterior spinal frame member to enable a user to adjustably apply a thoracic force with adjustable controlled buckles and straps positioned on the user's chest.

32 Claims, 9 Drawing Sheets

U.S. PATENT DOCUMENTS

| | | | |
|---|---|---|---|
| 5,704,937 A | 1/1998 | Martin | |
| 5,954,250 A * | 9/1999 | Hall et al. | 224/262 |
| 5,954,253 A * | 9/1999 | Swetish | 224/631 |
| 6,010,472 A | 1/2000 | Schiller | |
| 6,063,047 A | 5/2000 | Minne | |
| 6,190,343 B1 | 2/2001 | Heinz et al. | |
| 6,213,968 B1 * | 4/2001 | Heinz et al. | 602/19 |
| 6,790,191 B1 | 9/2004 | Hendricks | |
| 7,186,229 B2 * | 3/2007 | Schwenn et al. | 602/19 |
| 7,201,727 B2 | 4/2007 | Schwenn et al. | |
| 2005/0067816 A1 | 3/2005 | Buckman | |
| 2007/0152007 A1 * | 7/2007 | Kauss et al. | 224/637 |

OTHER PUBLICATIONS

Michael Pfiefer, MD et al.; "Effects of a New Spinal Orthosis on Posture, Trunk Strength, and Quality of Life in Women with Postmenopausal Osteoporosis—a randomized trial"; American Journal of Physical Medicine & Rehabilitation, vol. 83, No. 3, Mar. 2004, USA, pp. 177-186.

* cited by examiner

ADJUSTABLE EXTENSION COMPRESSION POSTERIOR SPINAL ORTHOSIS AND METHOD

BACKGROUND OF THE INVENTION

1. Field of the Invention

The present invention is directed to a lightweight brace or ortho praxis device and method for the treatment of patients with upper back pain, strain, osteoporosis and compression fractures and more particularly, to an easily worn and adjusted extension compression posterior spinal orthosis for applying extension and compressions forces in the treatment of spinal disorders.

2. Description of Related Art

Problems related with spinal disorders have been a bane of mankind, probably from the time that man started walking on two legs. Numerous different attempts have been made to provide an orthotic treatment to relieve pain and compensate for various types of spinal disorders such as multiple compression fractures that may occur from osteoporosis and kythotic postural changes.

Frequently, these spinal braces have employed a triangular or three point force vector system that includes an anchor point centrally located across the chest of the user which can be provided by a sternal pad supported, for example, by a metal frame and a corresponding anchor point on the lower portion of the abdomen, provided by a pubic pad supported by a frame. Thus, two forward pressure points are provided on the front of the user and a centrally located adjustable lumbar pad is provided on the user's back, again adjustably fixed to a metal frame so that three force vectors can be applied to create a condition of hyperextension on the spinal column, while permitting some mobility to the user. An example can be seen in the Jewett brace shown in U.S. Pat. No. 3,274,996.

Basically, this orthotic modality of treatment involves an anterior spinal hyperextension orthosis to create spaced anterior anchor stabilization points across the sternum and pubic areas with an adjustable force applied at an intermediate position on the user's back. Numerous variations of this treatment can be found, for example in U.S. Pat. No. 5,599,287, U.S. Pat. No. 6,190,343, U.S. Pat. No. 6,790,191, U.S. Pat. No. 6,010,472, U.S. Pat. No. 5,674,187, and U.S. Pat. No. 3,945,376. Other examples and variations can also be found in the orthodesic art.

An article in the *American Journal of Physical Medicine and Rehabilitation* "Effects of a New Spinal Orthosis of Posture, Trunk Strength And Quality of Life In Women With Postmenopausal Osteoporosis," Volume 83, No. 3, Pages 177-186, March 2004, described a study on the management of vertebra fractures caused by osteoporosis. A thoracolumbar orthosis disclosed in the study included a narrow back pad centered along the spine which could be workable as cold material to adjust to the particular patient, a system of belts, and an abdominal pad to apply lower, intermediate and upper forces on the back pad to mold it to the spinal region of the user. See U.S. Pat. No. 6,063,047. Also see U.S. Pat. No. 2,828,737.

There is still a need in the orthopedic field to provide a lightweight, comfortably wearing extension compression orthosis and method to treat mid spinal pathologies that does not require cumbersome strapping arrangements. Such a brace should be easily adjusted by the user to accommodate for various daily activity demands, to provide an improved, firm, lightweight posterior support structure that permits vector forces to be adjustably applied to the body by the user and to permit adjustments in the length of the orthosis to match the size and configuration of the user.

SUMMARY OF THE INVENTION

The present invention provides a lightweight spinal orthosis such as an adjustable extension compression posterior spinal brace that can be easily placed on the user's body while permitting the user to control and easily change how much extension and compression is desired for different daily activities of the user during the wearing of the spinal orthosis.

The present invention further provides a posterior spinal frame member that can be firmly anchored without requiring cumbersome sternum and pubic pads to facilitate a method of treatment.

The present invention permits a patient that may be in pain and in a frail condition because of age and/or postoperative circumstances, to don such a spinal orthosis and to remove it in a relatively easy manner.

The spinal orthosis can be easily adjusted by the user to thereby permit the user to accommodate different daily activities and to encourage the user to consistently use and receive the benefit of the spinal orthosis throughout the day. Thus, the present invention encourages user compliance while removing unsightly anterior sternum and pubic pads, and enables the spinal orthosis to be worn beneath clothing to relieve any uneasiness experienced by the user in his/her appearance in the public.

The spinal orthosis includes a lumbo-sacral compression unit incorporating a first body member conforming to a portion of the user's torso, a second body member conforming to another portion of the user's torso, and a closure unit, operatively connected to the first and second body members, for creating a compressive force about the user's torso, for example about the waist of the user, with a minimum of user effort. The closure unit provides a mechanical advantage so that a light force applied by the user can create significant encircling compression forces to create a hydraulic lift with corresponding beneficial effects to the spinal column and also firmly anchoring a posterior spinal frame member along the user's spine while distributing the compressive force around the entire waist of the user.

The spinal frame member can have an elongated triangular configuration with lateral semi-rigid plates extending outward from a rigid spinal frame member, which further has appropriate openings to minimize weight while maintaining a rigid configuration. The lateral semi-rigid plates can be bendable by the lumbo-sacral compression unit to firmly anchor the spinal frame member on the user's waist, when the compression force is distributed across the lower portion of the spinal frame member. The lateral semi-rigid plates are thin enough to eventually conform to the waist of the user after repeated applications of a compressive force during use.

Alternatively, the spinal frame member can be integrally formed, by plastic molding, with relatively movable lateral portions, for example in plastic with living hinges provided for connection between the curved lateral portions and a rigid spinal frame members to readily enable compliance with the shape of the user and a firm spreading of the compressive forces from the first and second body members.

A pair of adjustable shoulder strap assemblies are connected to an upper portion of the spinal frame member and also connected adjacent a lower portion of the spinal frame member, wherein the user can adjustably alter the position of the shoulder straps during use to optimize the extension of the shoulders and the upper back of the user.

Each one of the adjustable shoulder straps can include a first strap unit with a shoulder pad, adjustably connected to the upper portion of the spinal frame member, and a second strap unit also adjustably connected to the first strap unit and to the lower portion of the spinal frame member. The first strap unit can include a friction buckle member with the second strap unit including a strap connected to the lower portion of the spinal frame member and extending through the friction buckle member whereby the user can pull the extended straps downward on the sides of the chest for adjusting extension of the shoulder and upper back of the user, and can easily loosen the straps by relative movement of the buckle and pulling the strap forward away from the chest. Thus, by lifting a tab on the buckle, it is capable of releasing the tension and the buckle can be slid upward to provide less force and also an adequate opening for removing the orthosis.

Likewise, the lumbo-sacral compression unit can employ a tab or D-shaped ring which in combination with a hook and nap material such as Velcro™ permits an easy release of the encircling compression forces. Thus, during daily activities, relative adjustments applied by the lumbo-sacral compression unit and the shoulder strap assemblies can be easily accomplished by the user while wearing the spinal orthosis.

An orthotist can adjust the spinal frame member to the specific size and shape of the user and can also increase the length of the spinal frame with an adjustable extension in one embodiment.

The adjustable extension compression posterior spinal orthosis of the present invention can address, among other problems, Thoracic Compression Fractures, Kyphosis, Osteoporosis, Upper thoracic spine strain due to postural problems, and acute pain that can be relieved by thoracic extension.

The adjustable extension compression posterior spinal orthosis can extend the user's thoracic spine and unweight any wedged vertebral body in order to promote healing and pain relief. Our spinal appliance stabilizes the pelvis and lumbar spine with the compression belt component. The compression belt also serves as an anchor for the cantilevered posterior component. This anchor is more secure than the orthoses which are only strap based and do not have a level of pelvic compression. Also, the patient experiences a unique combination of pelvic and lumbar spine compression and stabilization along with the thoracic extension due to the custom contoured posterior cantilevered beam with shoulder straps to apply the thoracic extension load. Unique, anti-twist straps also make for a very simple don/doff that is similar to a backpack or jacket. The compression belt panels are also suspended with elastic straps so they can be held in just the right position to allow for simple don/doff without requiring the patient to reach behind and twist to find the panels.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

Reference will now be made in detail to the preferred embodiments of the invention which set forth the best modes contemplated to carry out the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well known methods, procedures, components, and materials have not been described in detail as not to unnecessarily obscure aspects of the present invention.

Figure 1:
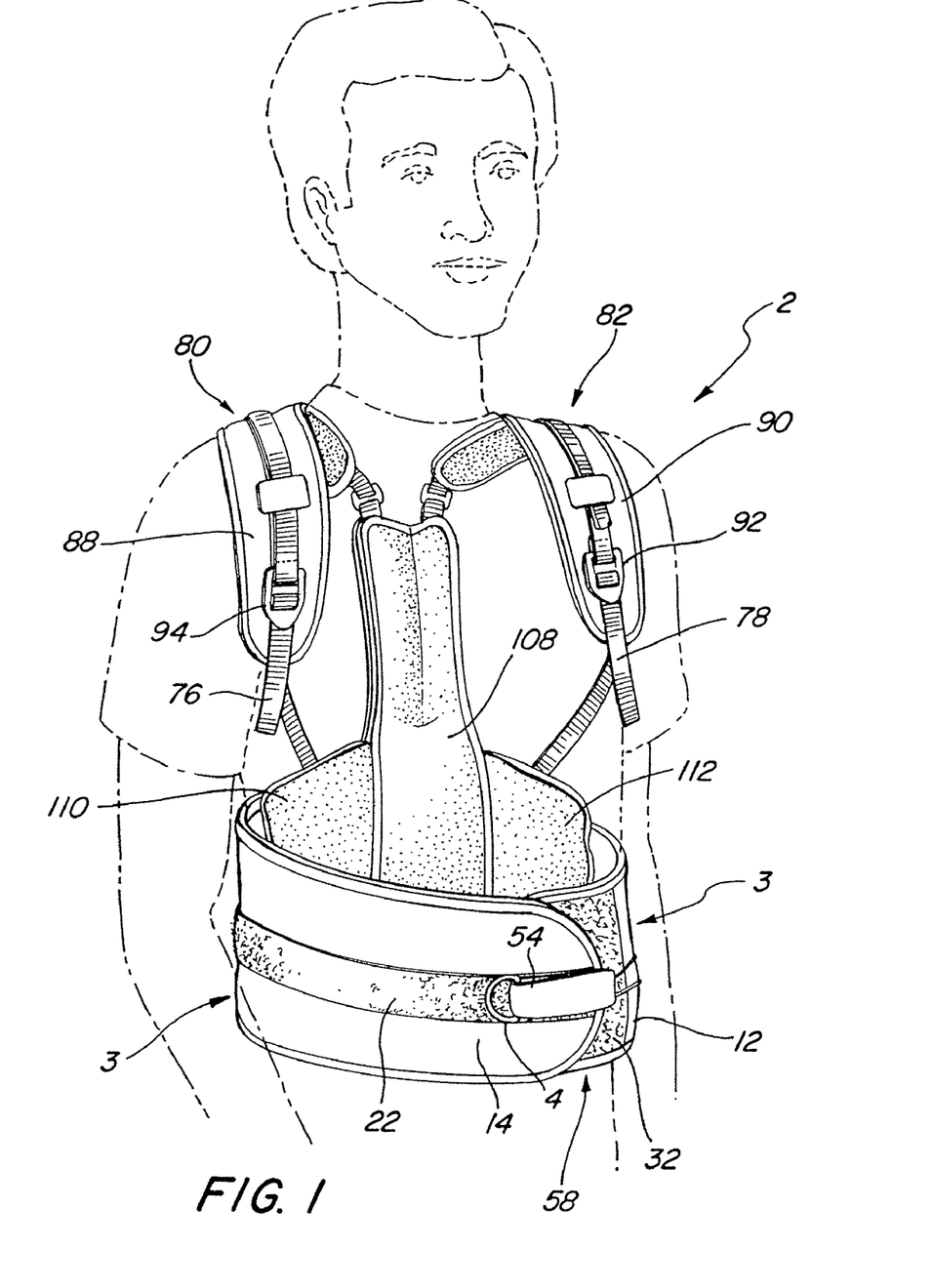
FIG. 1 is a front perspective view of the extension compression posterior spine orthosis of the present invention.

Referring to FIG. 1, an anterior frontal view of a extension compression spinal orthosis 2 of the present invention is disclosed in a manner that would be initially operatively positioned on a user or patient. The actual position on the user is not completely to scale and will vary, depending on the height, weight and body configuration of the user. Usually a doctor or an orthotist will initially adjust the pre-fabricated spinal orthosis to fit the user.

A lumbo-sacral compression unit 3 permits a user to provide compressive forces about his/her torso by simply pulling and removably fastening a fastener member 4 to a surface portion of the orthosis. The applied force can be distributed evenly about the lower torso or waist of the user and creates a hydraulic lift effect to help relieve pressure on the spinal column.

Figure 2:
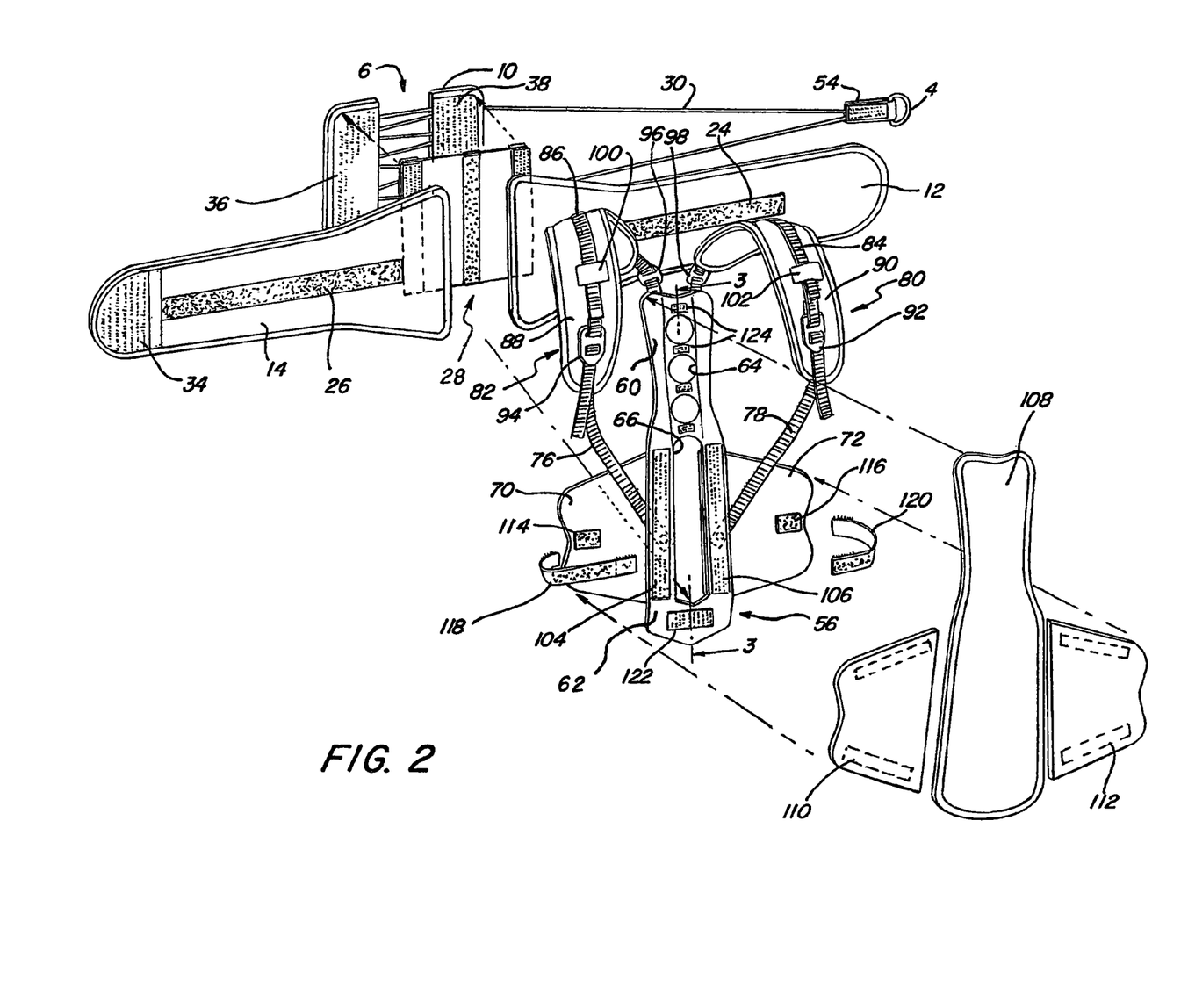
FIG. 2 is an exploded perspective view of FIG. 1.
Figures 5, 7:
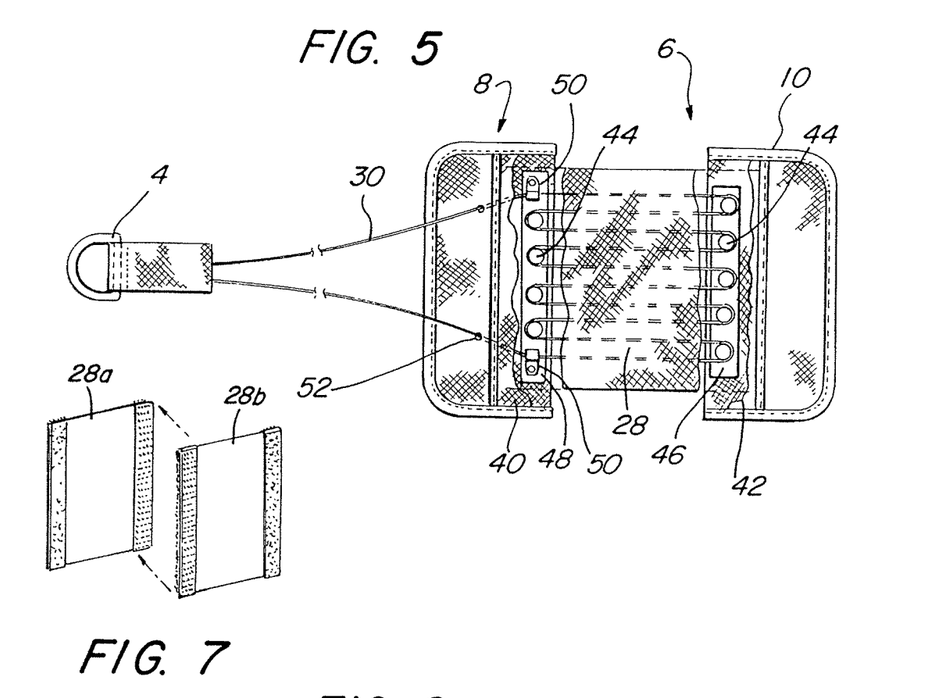
FIG. 5 is a rear view with a partial cutaway of the closure unit.
FIG. 7 is an exploded view of a two part elastic band.
Figure 6:
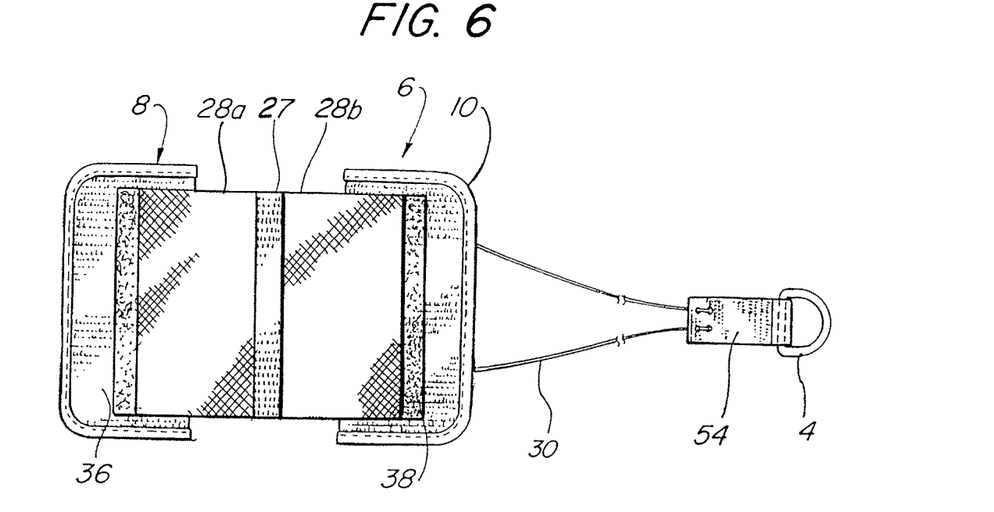
FIG. 6 is an opposite side view from FIG. 5 of the closure unit.

As can be seen in FIGS. 5 and 6, a closure unit 6 mounted on the rear posterior side, as shown in FIG. 2, can include a first connector member 8 and a second connector member 10. A first body member 12 and a second body member 14 are capable of conforming to a portion of the user's torso, such as the waist of the user. Preferably, the first body member 12 and the second body member 14 are made with a porous material such as an extra firm polyester from Gehring Textiles, Inc. of Garden City, N.Y. and nylon webbing to enable ventilation of the user's body through the respective body members 12 and 14.

Alternatively, stiffening support members (not shown) can be inserted into or on the respective body members 12 and 14, including, if necessary, an abdominal stay member, not shown. Such stay members can be inserted, for example, within pockets provided in the respective body members, or could be appended, for example, with a hook and nap material such as Velcro™ for appropriate location relative to the user on the interior surfaces of one or more body members. Thus, the basic spinal orthosis 2, shown in FIG. 1 can be customized with accessory parts to meet specific medical demands of a particular patient.

Figure 4:
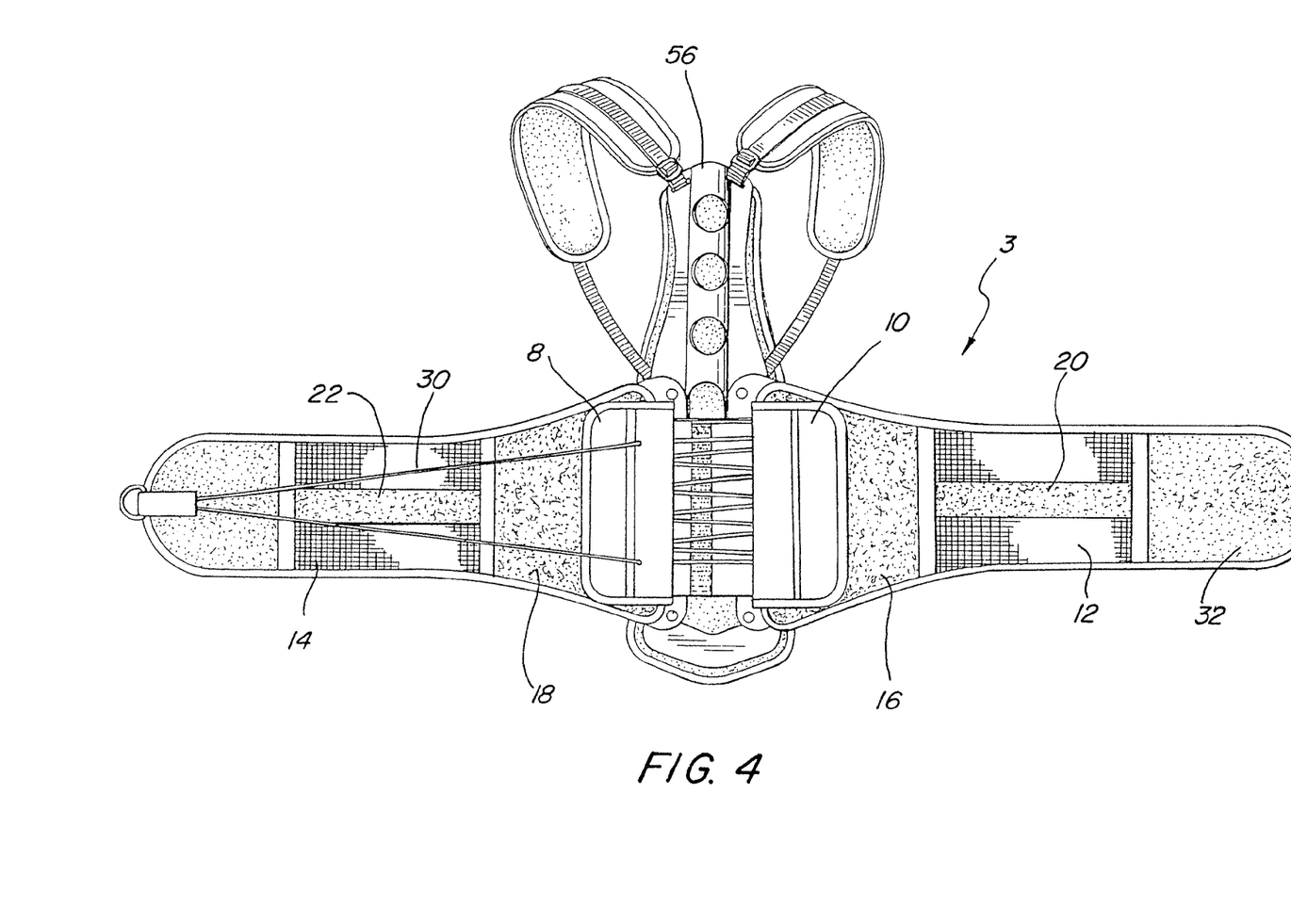
FIG. 4 is an elevated rear view of the present invention.

As shown in FIG. 1, the lumbo-sacral orthosis 2 has basically a wide belt-like configuration of approximately six inches in height that gradually increases to a posterior portion of approximately eight inches in height, although other dimensions can be used depending on the physical characteristics of the particular user, and the desire to provide a hydraulic lift. As can be seen in FIG. 4, the respective posterior ends have a nap material 16 on an exterior side of the first body member 12, and a nap material 18 on an exterior side of the second body member 14.

Additionally, an elongated rectangular strip or panel of nap material 20 is provided on the exterior of the first body member 12, and a similar elongated panel of nap material 22 is provided on the exterior of the second body member 14, as shown in FIG. 4. These respective strip or panel members 20 and 22 provide anchor points for a corresponding hook material 54, attached to the fastener member 4. The fastener member 4 as shown can be a plastic D ring that can be attached to a flexible elongated cord 30.

The cord 30 can be formed from a nylon material having an exterior braided surface to thereby provide a low friction but strong pull material, such as Dacron cord with a diameter of 0.042 inches and a 90 pound test strength.

Additional elongated strips or panels of nap material are also utilized on an interior surface, that is interior relative to being adjacent to a user's body. Thus, the first body member 12 has a strip of nap material 24 and the second body member 14 has a strip of nap material 26. These strips will be subsequently described in correlation with a posterior spinal frame member 56, as shown in FIG. 2.

A distal end of the first body member 12 has a semicircular patch of nap material 32 on the exterior surface. A distal interior surface of the second body member 14 has a patch of a semicircular configuration of hook material 34. Thus, these respective distal ends of the first and second body members, can be subjectively fastened about the waist of a user and they collectively form a fastener unit 58 to connect the first body member 12 to the second body member 14, on the front or anterior surface of the user.

Referring to FIGS. 5 and 6, the closure unit 6 includes fastener portions 36 on an underside of a hook material on the first connector member 8 and fastener portions of a hook material 38 on the second connector member 10. The respective hook members can be subjectively positioned to removably connect with the exterior nap material 18 on the second body member 14, and the nap material 16 on the exterior surface of the first body member 12.

As can be readily appreciated, the first connector member 8 and the second connector member 10 could alternatively be permanently fastened by rivets or stitching or otherwise to their respective body members.

The respective connector members 8 and 10 can be formed from a fabric material. However, alternative embodiments such as a plastic housing, which would either be permanently fastened or removably fastened on the respective body members can be used. The advantage of having hook and nap material permits subjective adjustment for both location and size of the user by the orthotist and also permits the closure unit to be removed so that the first body member 12 and the second body member 14 can be separately washed and cleaned, if necessary.

In FIGS. 5 and 6, the upper surface of the connector members 8 and 10 can include open support pockets 40 and 42 of a nylon webbing that can cover and house a plurality of plastic support posts 44 and loop material to which a lower base is sewn. The support posts 44 will extend perpendicular to an exterior surface of the user, when the first body member 12 and the second member 14 are appropriately fastened about the user. The support posts 44 can be formed, for example, of extruded plastic or alternatively can be arranged to be individual metal rivets between a pair of plates forming a housing for the support posts 44.

In the embodiment shown, the support posts 44 are respectively affixed to a base member 46. Each of the pockets 40 and 42 have an open slit to permit the cord member 30 to wrap around the respective support posts 44 in each of the connector members 8 and 10 to thereby provide a mechanical advantage or force multiplier when the cord 30 is pulled over the posts 44 by the user. As can be seen, the fastener member 4 is attached, for example, through the strip of hook material 54, directly to each end of the unitary cord 30. Because both ends of the cord 30 are respectively pulled, the distance of movement of the fastener member 4 about the waist of the user can be shortened while providing the desired hydraulic lift.

As can be appreciated, one end of the cord 30 could, alternatively, be anchored to one of the connector members and the pulling of the free end by the fastener member 4 can produce the same mechanical advantage of multiplying the force exerted by the user for pulling the posterior ends of the first body member 12 and the second body member 14 together, to create the compressive hydraulic lifting force on the user. The term "hydraulic lifting force" refers to the squeeze or compression of the waist of the user's body because of the flexible and fluid contents of the user's body. However, both ends of the cord 30 are preferably connected to the fastener member 4 to limit the hand movement of the user about his/her body when compared with only pulling one end of the cord 30.

As shown in FIG. 5, a base member 48 and the first connector member 8 can further have cord pull member guide eyelets 50 that permit the respective ends of the cord member 30 to be aligned so they can exit through ports 52 for attachment to the fastener member 4. One side of the fastener member 4, as shown in FIG. 6, includes a strip of hook material 54. The rear of the exterior panels 16 and 18 on the respective first body member 12 and second body member 14 shown in FIG. 4, permit a removable locking of the closure unit 6 and a subjective alignment on the respective body members 12 and 14 to meet the subjective demands of the individual user or patient. The user, after pulling upon the fastener member 4, can appropriately adhere the hook material strip 54 to either one of the strips of nap material 22 or 20, to maintain the appropriate compressive force. Because of the mechanical advantage, a user could be relatively feeble and still exert a significant compressive force with relatively little effort.

The ability of the cord 30 to slide with low friction across the respective support posts 44 provides a relatively compact and efficient mechanical advantage without requiring additional moving parts, such as pulleys. Alternatively, pulleys could be used in an alternative embodiment if necessary The individual support posts 44 can comprise a rivet assembly having either a sufficient smooth outer surface or the body of the rivet can be mounted within a sleeve that is fixed and gauged by a rivet when it is attached to its appropriate base material to extend perpendicularly upward. Preferably, an economically produced series of posts and housing components can be manufactured from plastic. The nylon cord 30 having a low coefficient of friction can appropriately slide across the surface of the posts regardless of the material of which it is made.

Figure 3:
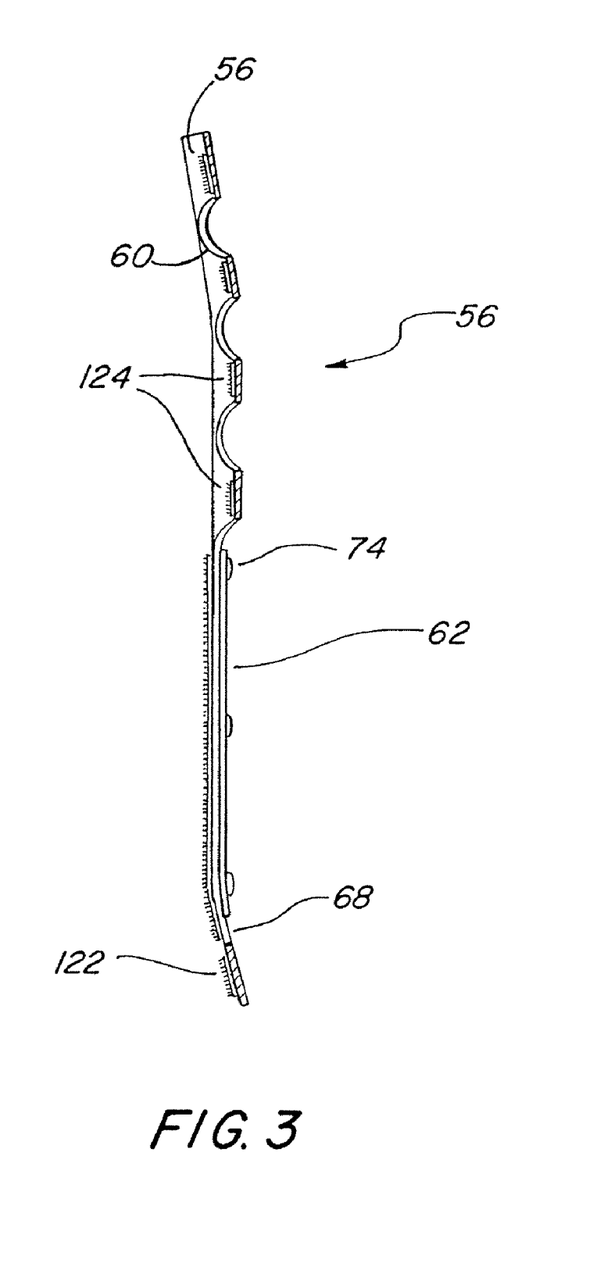
FIG. 3 is a cross-sectional view taken along line 3-3 of FIG. 2.

Referring to FIG. 3, the posterior spinal frame member 56 is formed from a lightweight material such as an aluminum alloy, and has an upper frame portion 60 and a lower frame portion 62. An orthotist can subjectively bend the frame member 56 to adjust to the particular physiological characteristics of the patient.

The upper frame portion has side concave edges from a moderately enlarged upper end of about 3 inches in width. The upper end includes oblong slots of about 1⅛ inch in length for receiving 1 inch wide nylon web straps as shown in FIG. 4, to be described subsequently. A series of circular holes of 1⅝ inches in diameter can be placed in the upper frame portion 60 to lower the weight.

As seen in FIGS. 2 and 3, a central outwardly curved channel of about 2 inches in width and ½ inch in depth terminating in a 6¼ inch width is provided on the upper frame portion to further add strength. The holes 64 also facilitate the bending of the upper frame portion 60 by the orthotist to adjust the shape of the spinal frame number 56 to the patient's spine. The curved channel of the upper frame portion 60 accommodates a clearance to allow for vertebral prominence on elderly patients. The upper and lower frame portions 66 and 62 provide an approximately elongated U-shaped contact surface that is to be aligned on either side of a user's spinal column.

The lower frame portion 62 has a slight triangular configuration with a corresponding elongated central opening 66 terminating in a peaked lower portion. The opening 66 gradually increases from 1½ inch in width at the top to 2¼ inch in width at the bottom. The bottom frame portion 68 can be bent away from the user to both prevent any body interference and to provide some additional strength.

A pair of lateral semi-rigid plates 70 and 72 can be affixed to the respective sides of the lower frame portion 62, for example, by rivets. The plates can be formed of plastic and are capable of being conformed to the lower back of the user when the closure unit 6 exerts a compressive force through the first and second body members 12 and 14.

A cross-sectional view is shown in FIG. 3 with the rivets 74. Additionally, a rivet can also extend through the lower frame portion on either side of the elongated opening 66 to affix flexible straps 76 and 78, which form components in a pair of adjustable shoulder strap assemblies 80 and 82. A respective first strap 84 and 86 are each journaled in the oblong openings at the top of the spinal frame member 56. A portion of each of the straps 84 and 86 are sewed onto a central portion of the respective shoulder pads 88 and 90.

The lower portion of each of the first and second straps are looped and sewed to be anchored at a lower portion of the shoulder pads and to secure the respective buckles 92 and 94 such as a Tri-Glide buckle from Hi Tex Corp. The upper end of the respective straps 76 and 78 are looped through the buckles 92 and 94, and a free end of each of the respective straps 84 and 86 extend downward from the buckles so that the user can pull the strap to tighten the shoulder pads 88 and 90 across the shoulders of the user and thereby exert a force pushing the user's back and shoulders against the posterior spinal frame member 56. Lifting a lower tab on the respective buckles 92 and 94 can release the friction grip on the respective straps 78 and 76 to permit an easy adjustment of tension forces and a further opening of the loop of the adjustable shoulder strap assemblies 80 and 82 can provide an enlarged opening for removing the orthosis. Appropriate buckles 96 and 98 can permit further adjustment of the sizing of the first straps 84 and 86 and the free end of these straps can be appropriately retained, for example by a Velcro™ adjustable loop members 100 and 102.

The Velcro™ strips 104 and 106 can be adhered to the sides of the bottom frame portion 68 and individual patches of Velcro™ hook strips 124 can be placed between the holes 64 in the upper frame portion 60, with also a Velcro™ hook strip 122 on the bottom frame portion 68, to thereby adhere to a pad 108 configured to cover the posterior spinal frame member 56. A spinal frame member pad 108 has a nap surface which can be removably attached to a hook material of a Velcro™ type. Supplemental foam pads 110 and 112 have a configuration to match the respective lateral semi-rigid plates 70 and 72. Adhesive straps can be used to attach the plate pads 110 and 112 directly to the respective semi-rigid plates 70 and 72.

As seen in FIG. 2, a square of nap material 114 and 116 is adhered respectively to the semi-rigid plates 70 and 72. Straps 118 and 120 with a combination of nap and hook material can be connected respectively to the square nap material patches 114 and 116 and can be bent to extend behind the respective lateral semi-rigid plates 70 and 72. Preferably, the respective straps 118 and 120 are centered at the lower point of the concave edges of the semi-rigid plates 70 and 72 so that the hook material can fasten to the respective first body member 12 and the second body member 14 by interacting with the respective straps of nap material 24 and 26.

This arrangement provides a relatively movable interconnection of the posterior spinal frame member 56 to the first body member 12 and the second body member 14 in the lumbo-sacral compression unit 3. As a result, when closure unit 6 is activated or released, the respective first body member 12 and second body member 14 can extend towards or away from each other and the posterior spinal frame member 56 would permit such movement while still being appropriately aligned relative to the lumbo-sacral orthosis compression unit 3.

Also, when the user removes the extension compression spinal orthosis 2, the mounted posterior spinal frame member 56 will maintain its relationship to the lumbo-sacral compression unit orthosis 3 and be positioned for easy placement again onto the user.

The closure unit is shown in FIG. 5 with a flexible elastic band 28 to also permit relative movement and to assist in preventing entanglement of foreign objects in the draw cord 30.

As an alternative embodiment, the elastic band 28 can actually be split into two separate small bands 28a and 28b having appropriate strips 27 on each side edge of each of the respective elastic bands 28a and 28b with nap material on one side and a hook material on the other side, see FIG. 7. As shown in FIG. 6, the nap material is connected with the hook material 27 and similar strips obscured by the respective first connector member and the second connector member can be inserted between the connector members and the nap material respectively 16 and 18 as shown in FIG. 4 on the first body member 12 and the second body member 14 and between the hook material 36 and 38.

In FIGS. 2 and 4, the elastic band material 28a and 28b are used to directly close the gap between the respective ends of the first body member 12 and the second body member 14. As shown in FIG. 5, the elastic band 28a can be positioned on the exterior side to cover the cord 30 to prevent it from being entangled with foreign objects.

As can be readily appreciated, pairs of elastic bands 28a and 28b could encompass both the interior and exterior side of the cord 30 between the first connector member 8 and the second connector member 10.

Referring to FIG. 2, an orthotist can appropriately size, and if necessary bend the posterior spinal frame member 56 to the particular needs of the patient. Generally an orthotist will order a pre-fabricated brace by specifying a particular patient size such as large, small, etc., and then can adjust the brace to customize it for the particular patient.

The pads 110 and 112, shown in FIG. 2, can be appropriately adhered by strips of adhesive to the sides of the lateral semi-rigid plates 70 and 72 while still permitting access to insert the straps 118 and 120 for connection with the square nap material 116 and 118 on the respective semi-rigid plates 70 and 72. The spinal frame pad 108 can then be adhered to the strips of hook material 104 and 106, the rectangular patch of hook material 122 and the small patches of hook material 124 on the upper frame portion 60. The reverse side of the pad 108 has an appropriate cloth nap configuration that permits removable adherence while also permitting the pad 108 to be periodically washed for sanitary purposes when it is removed.

The orthotist can also appropriately adjust the respective pair of adjustable shoulder strap assemblies 80 and 82 and can cut the free ends of the first straps 84 and 86 to provide enough of an extension for the user to grab and adjust for his/her body size. As can be appreciated, a D-shaped ring could also be attached to the end of the straps after the adjustment by the orthotist to further facilitate an easy adjustment by a user during daily activities. The orthotist will usually teach a patient how to lift the front tab of the respective buckles 94 and 92 for releasing the free ends of the straps 76 and 78. The orthotist can also adjust the shoulder pads 88 and 90. The first strap 84 and 86 with the shoulder pads 90 and 88 can be appropriately connected to the upper portion 60 of the spinal frame member 56 for the particular patient.

The orthotist will also appropriately fit and adjust the lumbo-sacral orthosis 3 including in an embodiment where the closure unit 6 is removable, the position of the first connector member 8 and the second connector member 10 on the respective nap material 16 and 18 at the rear of the first body member 12 and the second body member 14. Connecting the first and second body member 12, 14 with the closure unit 6 forms a unitary lumbo-sacral compression unit to extend around a user's torso. Additionally, the length of the cord 30 will be appropriately adjusted so that the fastener member 4 can have its hook material strip 54 fastenable on the anterior side of the patient.

Figure 8:
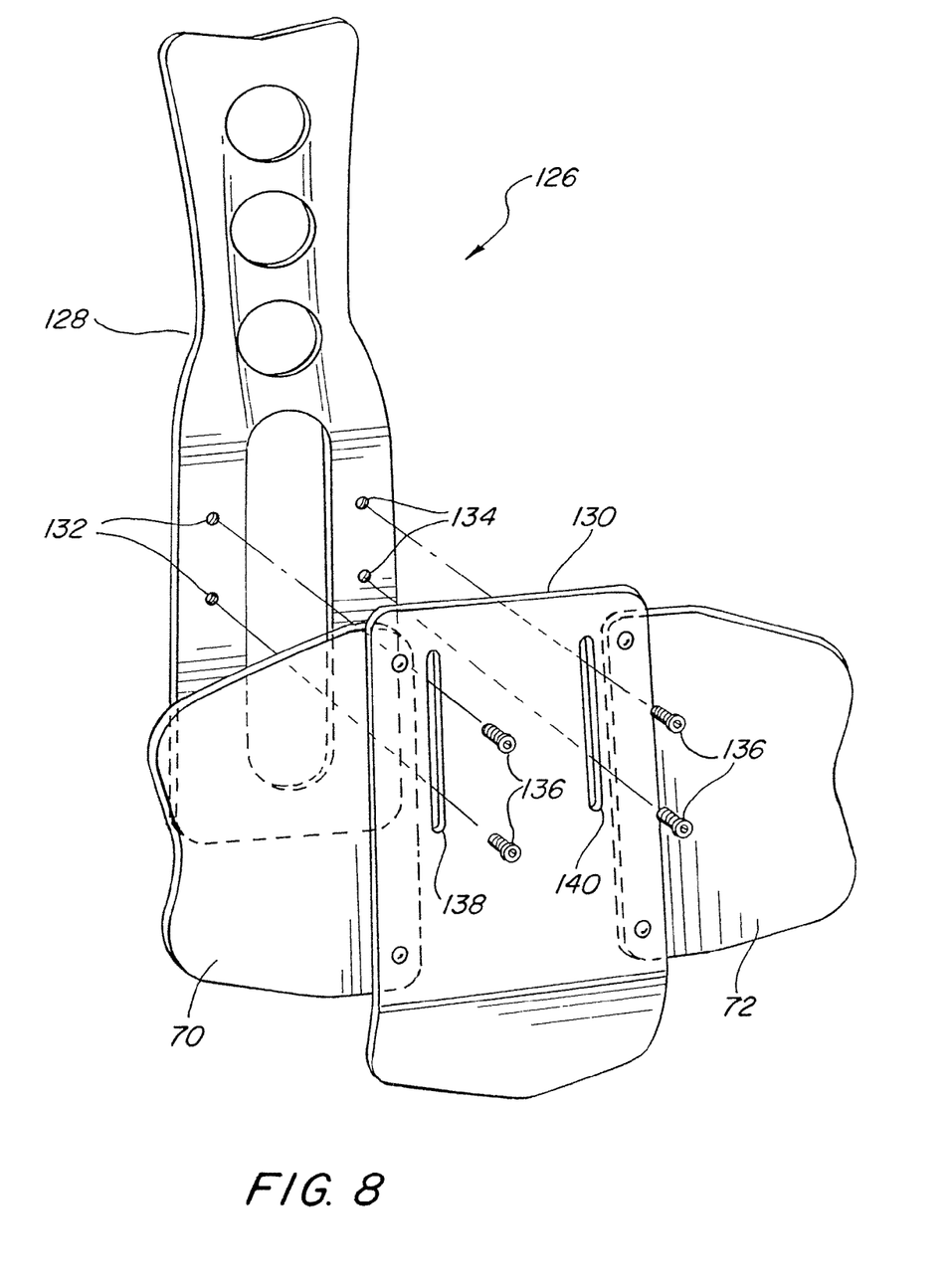
FIG. 8 is an exploded view of an adjustable spinal frame.

Referring to FIG. 8, an adjustable spinal frame member 126 has a plurality of holes 132 and 134 in the lower portion of the spinal frame column 128 which can receive fasteners 136 such as screws, rivets and the like for fixedly securing the base spinal frame column 128 and an adjustable lower spinal extension member 130 at an appropriate position to match the length of a user's spine. Elongated slots 138 and 140 in the spinal extension member 130 permit a relative alignment or adjustment to the length of the user's spine column by moving the extension member 130 along the spinal frame column 128.

The spinal extension member 130 can mount the lateral semi-rigid plates 70 and 72 with appropriate rivets. Spinal extension member 130 can be formed from an aluminum plate or alternatively from a relatively rigid plastic plate.

Figure 9:
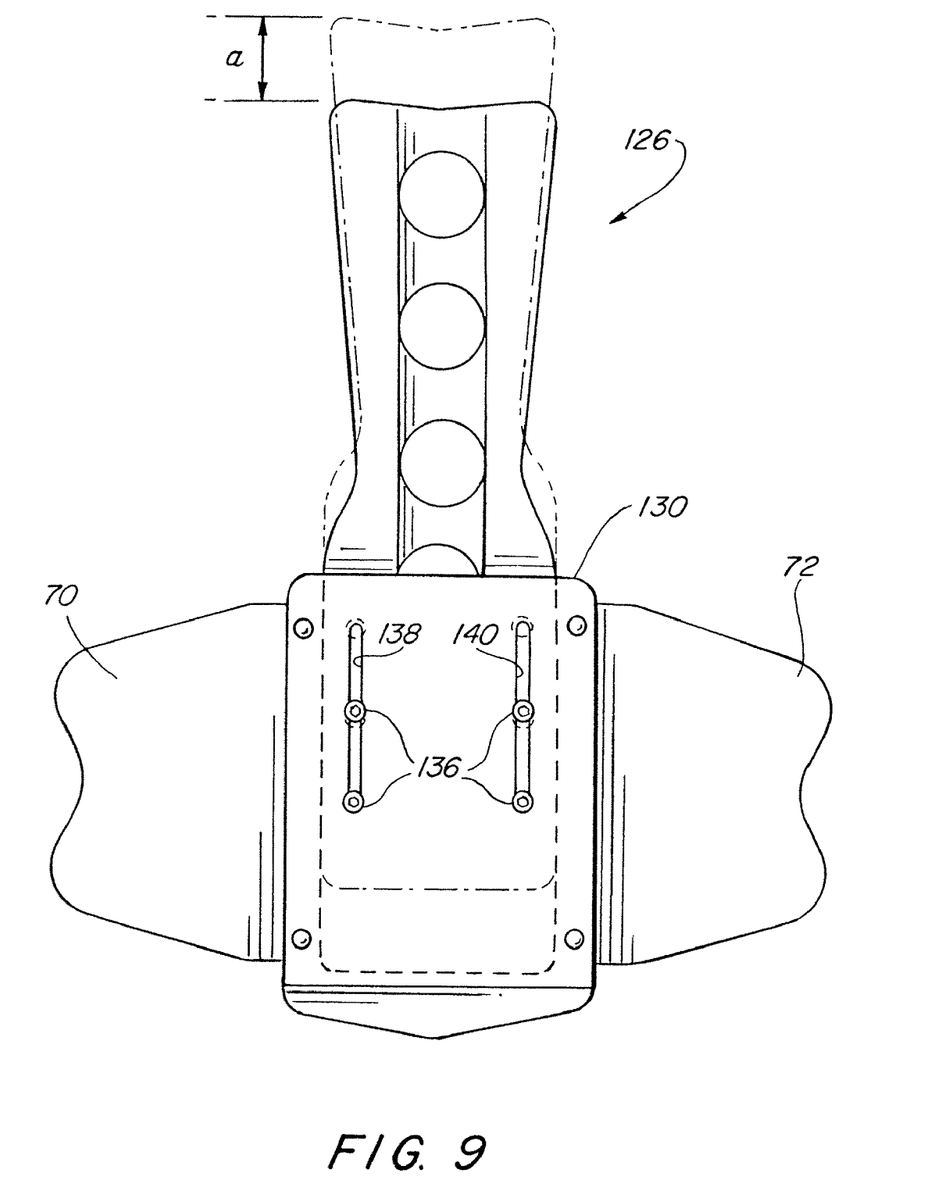
FIG. 9 is an assembled elevated rear view of the spinal frame of FIG. 8.

As shown in FIG. 9, an adjustment, a, of the overall length of the spinal frame member 126 can be easily accomplished, thereby reducing the requirement of providing different pre-fabricated sizes to the orthotist and thus limiting the inventory requirements on the manufacturer.

Figure 10:
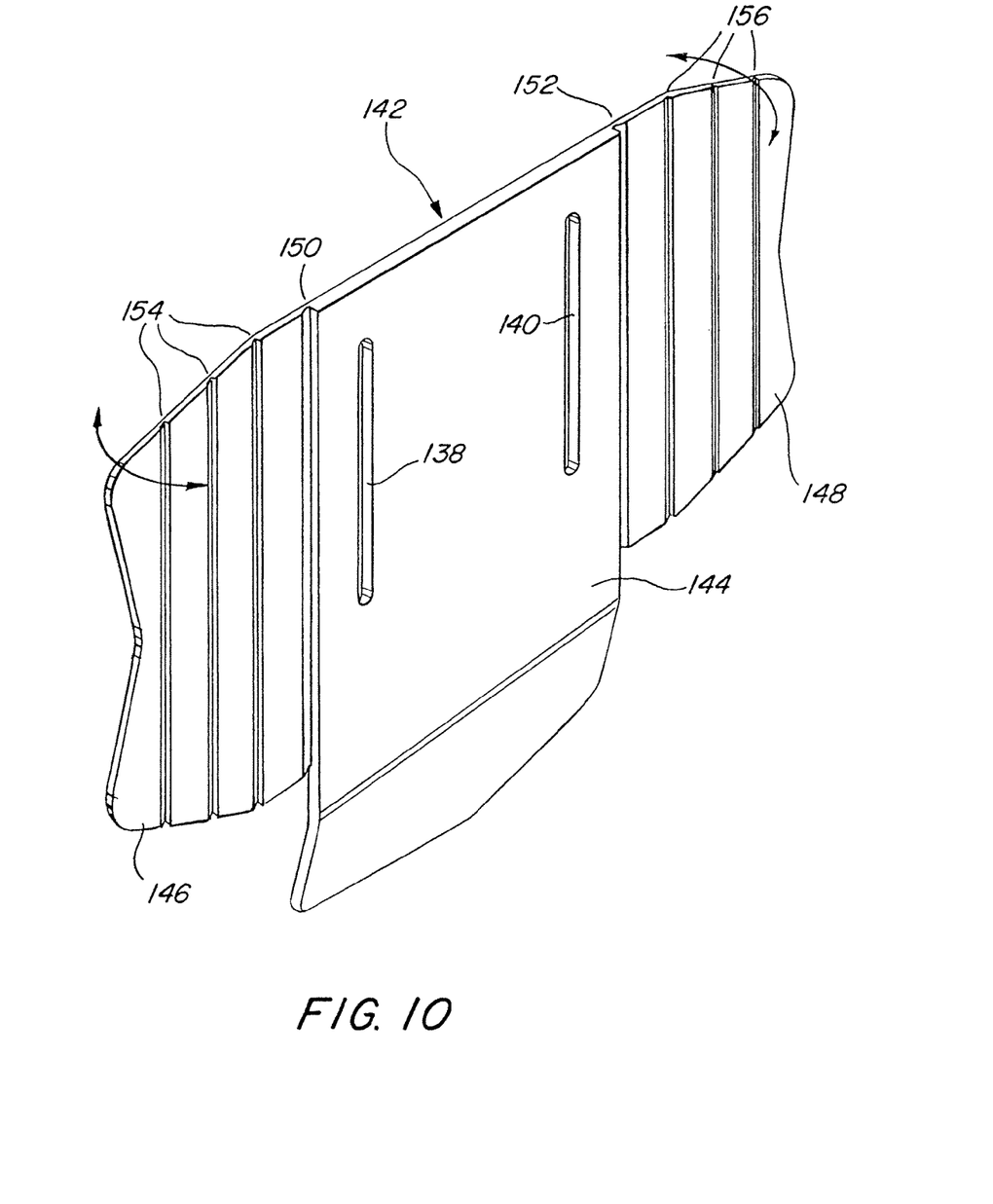
FIG. 10 is a modified spinal extension member.

FIG. 10 discloses a further modification of an integrated spinal extension member 142 that can be molded from plastic with a thicker and more rigid central plate 144 when compared with thinner and flexible lateral 146 and 148 connected to the central plate 144 by first living hinges 150 and 152.

The living hinges 150 and 152 are formed integrally in the plastic molding process by providing grooves of a narrow thickness that enable relative movement of each lateral side plate 146, 148 relative to the more rigid central plate 144 to align the molecules of the plastic to enable while still held repetitive pivotal movements. The lateral plates 146, 148 can further bend to conform to the user's waist and enable a further distribution of the compression forces from the lumbo-sacral orthosis 3. By providing a series of parallel second living hinges 154 in lateral side plate 146 and a series of parallel second living hinges 156 in lateral side plate 148 the respective lateral side plates 146 and 148 can easily conform to the user's waist size by bending relative to the spinal column while still maintaining a significantly rigid configuration of longitudinal support. Additionally, the lateral side plates 146 and 148 can be adjusted by cutting distal portions or edges along the living hinge grooves to adjust for the patient's waist size.

As can be appreciated by an orthotist, the extension compression spinal orthosis 2 of the present invention, can stably position the posterior spinal frame member 56 so that it can be firmly aligned with the spine of the user. The lower frame portion 62 and the lateral semi-rigid plates 70 and 72 receive a compressive force from the lumbo-sacral orthosis 3 with concave end portions engaging the respective first body member 12 and the second body member 14, while providing an expanded application of force across the lower back of the user. At the same time, the first body member 12 and the second body member 14 are still relatively movable for applying and releasing the compressive force, and through straps 118 and 120, maintain a relative relationship with the posterior spinal frame member 56, even when the lumbo-sacral orthosis 3 is released and the extension compression spinal orthosis 2 is removed from the patient.

The compressive force of the lumbo-sacral orthosis 3 will be evenly distributed around the waist of the user to both prevent a localized application of a high force at one point on the user's waist and back and also to provide a hydraulic lift on the spinal column. The spinal frame member 56 is, accordingly, firmly anchored to be cantilevered upward along the spinal column from the user's waist.

Adjustment of the respective free ends of straps 76 and 78 on the lower second strap units can pull the shoulders of the user back against the upper portion of the spinal frame member 56. The user will not have significant constriction across his/her chest that would impair breathing and can readily adjust the spinal orthosis 2 for example, to accommodate sitting or other motions with relatively easy adjustments. Accordingly, our design encourages prolonged usage to ensure the user receives the benefits of a remedial extension compression orthosis.

Additionally, the lumbo-sacral orthosis 3 can be easily disassembled from the extension compression spinal orthosis 2 and used independently as a functional lumbar spinal orthosis. The strap configuration of this design also provides an anti-twist operation to assist users with limited shoulder mobility. Likewise, our padded shoulder strap design can loosen without completely unfastening in order to facilitate an uncomplicated reapplication to the user. The spinal frame member 56 is preferably made from aluminum but other metals and a plastic molded or plastic composite frame could be used. A Cool Foam™ can be applied as removable and washable pads to extend from the thoracic area to the symphysis pubis.

Figure 11:
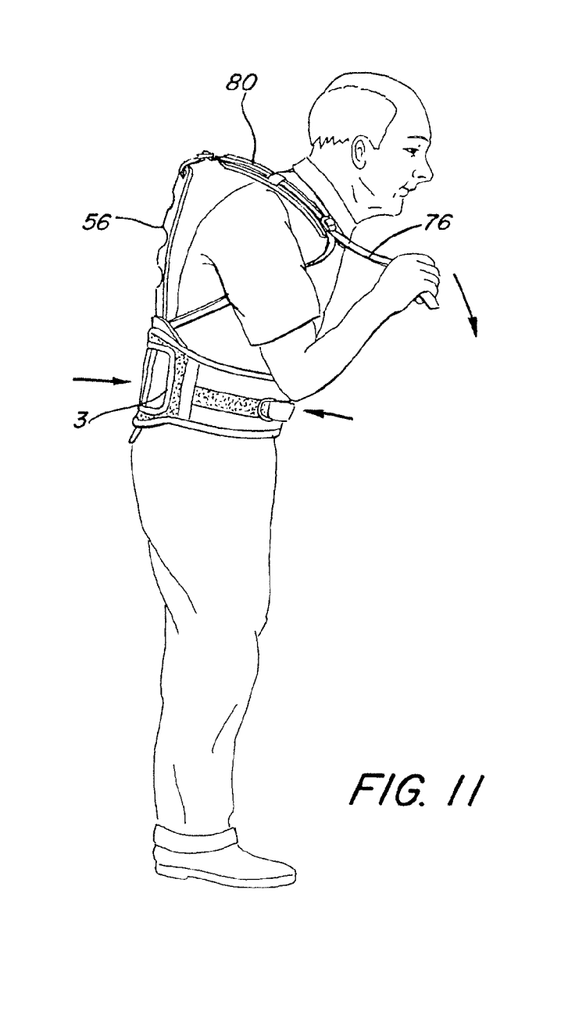
FIG. 11 is a schematic illustration of initially applying the extension compression spinal orthosis on a user.

Referring to FIG. 11, a schematic view of a user of the present invention, such as a patient suffering from osteoporosis with a bent spinal column has donned the extension compression spinal orthosis 2 of the present invention and has tightened the lumbo-sacral compression unit 3 to enable the posterior spinal frame member 56 to be cantilevered upward along the user's spinal column. The adjustable shoulder strap assemblies 80 and 82 are loosely positioned across the user's shoulders with an adjustable strap and buckle combination available on the respective right and left hand side of the chest of the user.

Figure 12:
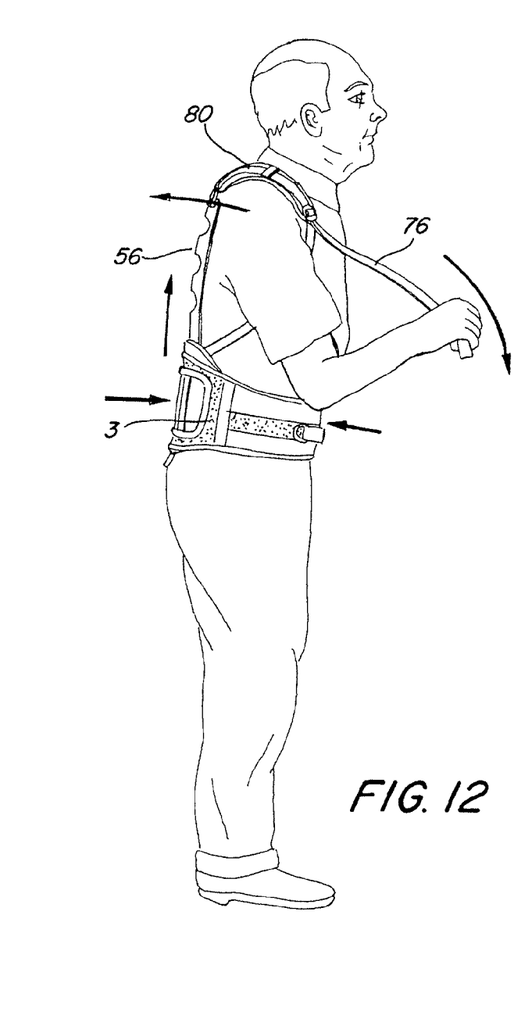
FIG. 12 is a schematic illustration of a user adjusting the thoracic extension force.

As shown, the user can grasp the free end of the strap 76 and 78 extending through the respective buckles 94 and 92 and by pulling downward as shown in FIG. 12, can extend the user's shoulder and upper back to contact the cantilever posterior spinal frame member 56. Thus, a thoracic extension force can be applied to each of the shoulders of the user to force the user's shoulders towards the posterior spinal frame 56 and thereby extend the user's spinal column as shown in FIG. 12. By releasing the hold of the buckles, the straps can be loosened to adjust the desired force for the user. As a result, the user experiences a uniformly distributed compression force around his/her waist to assist in a hydraulic lift of his/her spinal column while at the same time anchoring the posterior spinal frame member 56 to permit the shoulder pads 88 and 90 in the adjustable shoulder strap assemblies to exert a rearward thoracic support for straightening the user's spine.

Accordingly, the extension compression spinal orthosis 2 of the present invention permits the user to directly apply appropriate extension and compression forces to the user's spine with a wearable posterior spinal orthosis. The extension compression spinal orthosis 2 of the present invention is easily adjusted by the user to encourage extended use and can be easily removed and reapplied. The user's arms are not encumbered by any apparatus pressing across his/her chest. The lumbo-sacral compression unit 3 provides a mechanical advantage to exert an even distribution of compression force about the waist of the user with minimal effort.

Those skilled in this art will appreciate that various adaptations and modifications of the just-described preferred embodiments can be configured without departing from the scope and spirit of the invention. Therefore, it is to be understood that, within the scope of the amended claims, the invention may be practiced other than as specifically described herein.

What is claimed is:

1. A spinal orthosis comprising:
  a lumbar-sacral compression unit including
    a first body member conforming to a portion of a user's torso,
    a second body member conforming to another portion of a user's torso, and
    a closure unit operatively connected to the first and second body members for exerting a compressive force on the user's torso through the first and second body member;
  a posterior spinal frame member, configured to provide a remedial corrective shape for the user's spinal column, has a lower portion secured by the lumbar-sacral compression unit to enable positioning of the posterior spinal frame member, along and offset at a distal end from the user's spine; and
  a pair of adjustable shoulder strap assemblies connected to an upper portion of the posterior spinal frame member and adjacent the lower portion of the posterior spinal frame member wherein the user can adjustably apply a compression force about a waist portion of the torso with the closure unit to fix the distal end of the posterior spaced frame offset from the user's spine and can adjust the pair of adjustable shoulder strap assemblies to extend the shoulders and upper back of the user until contact with the distal end of the posterior spinal frame member to align the user's spinal column into an orthopedic corrective position against the posterior spinal frame member.

2. The spinal orthosis of claim 1 wherein the spinal frame member has a lower triangular configuration.

3. The spinal orthosis of claim 2 wherein the spinal frame member has a central oblong opening.

4. The spinal orthosis of claim 1 wherein a pair of lateral semi-rigid plates extend outward from posterior spinal frame member, the pair of lateral semi-rigid plates are bendable by the lumbar-sacral compression unit to anchor the lower portion of the posterior spinal frame member on the user's waist.

5. The spinal orthosis of claim 4 wherein the semi-rigid plates are formed of plastic.

6. The spinal orthosis of claim 5 wherein the semi-rigid plates are removably fastened to the respective first and second body members.

7. The spinal orthosis of claim 6 wherein distal ends of the semi-rigid plates each have a concave shape.

8. The spinal orthosis of claim 5 wherein the semi-rigid plates progressively narrow in width as each plate extends outward from the spinal frame member.

9. The spinal orthosis of claim 1 wherein each adjustable shoulder strap assembly includes a first strap unit with a shoulder pad connected to the upper portion of the spinal frame member and a second strap unit adjustably connected to the first strap unit and to the lower portion of the spinal frame member.

10. The spinal orthosis of claim 9 wherein each first strap unit includes a friction buckle member and each second strap unit includes a strap connected to the lower portion of the spinal frame member and extending through the friction buckle member whereby the user can pull the strap for adjusting an extension of the shoulder and upper back of the user.

11. The spinal orthosis of claim 1 wherein the closure unit has a first connector member with a first plurality of support posts operatively connected to the first body member, the first plurality of support posts are fixed and have axes extending approximately perpendicular to the surface of the first body member, a second connector member with a second plurality of support posts operatively connected to the second body member, the second plurality of support posts are fixed and have axes extending approximately perpendicular to the surface of the second body member, and an elongated flexible pull member operatively extending between the respective first and second support posts to provide a mechanical force advantage when tightened by the user in moving the first body member and second body member to conform about and against the user's torso.

12. The spinal orthosis of claim 1 further including a spinal pad member removably connected to the posterior spinal frame member.

13. The spinal orthosis of claim 12 further including a plate pad member removably connected to each respective semi-rigid plate.

14. The spinal orthosis of claim 1 wherein the posterior spinal frame member is formed of a metal with a central oblong opening in the lower portion and a series of central hole openings in the upper portion of the posterior spinal frame member.

15. The spinal orthosis of claim 1 further including a spinal extension member that is adjustably mounted on the posterior spinal frame member to provide an adjustable extension of the posterior spinal frame member to fit a user's size.

16. The spinal orthosis of claim 15 wherein the spinal extension member including a pair of lateral semi-rigid plates that extend laterally outward to engage and be bendable by the lumbar-sacral compression unit to anchor the lower portion of the posterior spinal frame member, and enable the posterior spinal frame member to be cantilevered adjacent the user's upper back from the user's waist.

17. The spinal orthosis of claim 16 wherein the spinal extension member includes an integrally molded plastic central plate with the lateral semi-rigid plates connected by first living hinges to the central plate to enable a pivotal bending to accommodate a user's waist size.

18. The spinal orthosis of claim 17 wherein a plurality of second living hinges are provided on each lateral semi rigid plate to facilitate a bending to accommodate a user's waist size.

19. The spinal orthosis of claim 1 wherein the upper portion of the posterior spinal frame includes a plurality of holes to facilitate a bending of the upper portion to customize the shape for the user.

20. The spinal orthosis of claim 1 wherein the posterior spine frame member is cantilevered upward and offset from the user's spinal column to terminate at the rear of the user's shoulders, the posterior spine frame member is configured into an orthopedic curved corrective position relative to the user's spinal column whereby a thoracic extension force applied through the pair of adjustable shoulder strap assemblies force the user's spinal column to align with the orthopedic curved corrective position of the posterior spine frame member.

21. The spinal orthosis of claim 20 wherein each adjustable shoulder strap assembly includes a first strap unit with a shoulder pad connected to the upper portion of the spinal frame member of a configuration to extend across the user's shoulder and overlay a portion of the user's chest with a first strap connected to the upper portion of the spinal frame member, the shoulder pad and a releasable buckle member positioned at the distal end of the strap, and a second strap unit including a strap connected to the lower portion of the spine and extending through the releasable friction buckle member to enable the user to pull the strap to exert the thoracic extension force to adjust an extension of the shoulder and upper back of the user as the user's spinal column is forced into a corrective alignment adjacent the posterior spine frame member.

22. A method of applying extension and compression forces to a user's spine in a wearable posterior spinal orthosis having a lumbar-sacral compression unit of a configuration to be adjustably mounted about a portion of a user's torso and a posterior spinal frame member extending upward from the lumbar-sacral compression unit to an orthopedic corrective position for a user's spine comprising the steps of;
configuring the posterior spinal frame member to provide an orthopedic corrective configuration appropriate for the user's spine;
positioning the spinal orthosis on a user;
applying a hydro-lift compressive force with the lumbar-sacral compression unit about the user's waist to position the posterior spinal frame member cantilevered from the lumbar-sacral compression unit upward and offset along the user's spinal column while distributing the compressive force around the user's waist to firmly fix the posterior spinal frame member offset from the user's spine in the orthopedic corrective position; and
applying a thoracic extension force on each of the user's shoulders to pull the posterior of the shoulders into a corrective contact with the posterior spinal frame to extend the user's spinal column in alignment with the posterior spinal frame member.

23. The method of claim 22 further including providing an adjustable control unit for each application of thoracic force on a chest of the user whereby the user can tighten and/or release the thoracic shoulder forces.

24. The method of claim 22 wherein the posterior spinal frame member is provided with a corrective curvilinear configuration to enable a corrective hyperextension of the user's spine when the thoracic exterior forces applied to the user's shoulders force the user's spine to conform to the corrective curvilinear configuration.

25. A spinal orthosis comprising:
a lumbar-sacral compression unit that is configured to adjustably encircle a user's waist and includes an elongated flexible pull member that can be fastened across a surface of the compression unit to provide a mechanical force advantage for a user to distribute compression forces about a portion of the user's torso by tightening the pull member and fastening the pull member at a desired compression force;
a posterior spinal frame member having a lower position overlapped by the lumbar-sacral compression unit to fixedly secure the posterior spinal frame member cantilevered upward from the user's waist to provide contact support at a position offset from the user's spinal vertebrae with an elongated U-shaped support surface that terminates at a distal end offset from and adjacent the shoulders of the user's upper back on an upper portion of the posterior spinal frame member, the U-shaped support surface is connected and supported by an outwardly curved channel that is configured to accommodate a vertebral prominence of the user; and
a pair of adjustable shoulder strap assemblies connected respectively to an upper portion of the posterior spinal frame member and a lower portion of the posterior spinal frame member whereby the user can releasably adjust the pair of adjustable shoulder strap assemblies, from positions adjacent the user's chest, to extend the shoulder and upper back of the user posteriorly to contact the fixed cantilevered posterior spinal frame member in an orthopedic corrective position for the user's spine.

26. The spinal orthosis of claim 25 wherein the posterior spinal frame member is a malleable metal member.

27. The spinal orthosis of claim 26 wherein the upper portion of the posterior spinal frame member has an upper end of approximately three inches in width.

28. The spinal orthosis of claim 27 wherein the curved channel has approximately a depth of 0.5 inch and a width of 2 inches.

29. The spinal orthosis of claim 28 wherein the curved channel has a plurality of holes of approximately 1.6 inches in diameter to lighten the posterior spinal frame member and increase the malleability to provide a particular physiological corrective position for the user's spine.

30. The spinal orthosis of claim 29 wherein each first strap unit includes a friction buckle member and each second strap unit includes a strap connected to the lower portion of the spinal frame member and extending through the friction buckle member whereby the user can pull the strap for adjusting an extension of the shoulder and upper back of the user.

31. The spinal orthosis of claim 26 wherein each adjustable shoulder strap assembly includes a first strap unit with a shoulder pad connected to the upper portion of the spinal frame member and a second strap unit adjustably connected to the first strap unit and to the lower portion of the spinal frame member.

32. The spinal orthosis of claim 25 wherein the lower portion of the posterior spinal frame member has a central elongated opening for alignment with the user's spine.

* * * * *